US00PP12139P2

(12) United States Plant Patent
Rother

(10) Patent No.: US PP12,139 P2
(45) Date of Patent: Oct. 9, 2001

(54) PETUNIA PLANT NAMED 'MARIPOSA ROSE'

(76) Inventor: Reinhard W. Rother, P.B. 327, Emerald, Victoria (AU)

( * ) Notice: Subject to any disclaimer, the term of this patent is extended or adjusted under 35 U.S.C. 154(b) by 0 days.

(21) Appl. No.: 09/545,908

(22) Filed: Apr. 9, 2000

(51) Int. Cl.[7] ..... A01H 5/00
(52) U.S. Cl. ..... Plt./356

(58) Field of Search ..... Plt./356

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Petunia plant named 'Mariposa Rose', characterized by its initially upright then low spreading and cascading plant habit; high vigor; freely and continuous branching growth habit; large leaves; relatively early flowering; and large reddish purple-colored flowers.

1 Drawing Sheet

BACKGROUND OF THE INVENTION

The present Invention relates to a new and distinct cultivar of Petunia plant, botanically known as *Petunia×hybrida*, and hereinafter referred to by the cultivar name Mariposa Rose.

The new Petunia is a product of a planned breeding program conducted by the Inventor in Emerald, Victoria, Australia. The new Petunia originated from a cross made by the Inventor of a proprietary selection of *Petunia×hybrida* identified as code number 131098 as the female, or seed, parent with a proprietary selection of *Petunia×hybrida* identified as code number 429 as the male, or pollen, parent. The new Petunia was selected in October, 1993 on the basis of its attractive flower color.

Plants of the new Petunia are more compact, more low spreading, and differ in flower color compared to plants of the female parent selection. Compared to plants of the male parent selection, plants of the new Petunia have larger flowers and also differ in flower color.

Asexual reproduction of the new cultivar by terminal cuttings taken at Emerald, Victoria, Australia, has shown that the unique features of this new Petunia are stable and reproduced true to type in successive generations.

SUMMARY OF THE INVENTION

Plants of the cultivar Mariposa Rose have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Mariposa Rose'. These characteristics in combination distinguish 'Mariposa Rose' as a new and distinct cultivar:

1. Initially upright then low spreading and cascading plant habit.
2. Freely and continuous branching.
3. High vigor.
4. Large leaves.
5. Relatively early flowering.
6. Large reddish purple-colored flowers.

Plants of the cultivar Mariposa Rose can be compared to plants of th cultivar Revolution Pinkvein, disclosed in U.S. Plant Pat. No. 9,341. However in side-by-side comparisons conducted by the Inventor in Emerald, Victoria, Austrailia, plants of the cultivar Mariposa Rose have larger flowers, larger leaves, and flower earlier than plants of the cultivar Revolution Pinkvein.

Plants of the cultivar Mariposa Rose can also be compared to plants of the cultivar Sunlace, disclosed in U.S. Plant Pat. No. 10,044. However in side-by-side comparisons conducted by the Inventor in Emerald, Victoria, Australia, plants of the cultivar Mariposa Rose and Sunlace differ in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Petunia.

The photograph at the top of the sheet comprises a side perspective view of typical flowering plants of 'Mariposa Rose'.

The photograph at the bottom of the sheet is a close-up view of a typical opened flower, a typical opening flower bud, and upper and lower surfaces of typical leaves of 'Mariposa Rose'.

DETAILED BOTANICAL DESCRIPTION

In the following description, color references are made to The Royal Horticultural Society Colour Chart except where general terms of ordinary dictionary significance are used. Plants grown in 25-cm containers were used for the following description with three or four plants per container. Plants were grown under full sun field conditions which closely approximate commercial production conditions during the spring in Bonsall, Calif. Day temperatures ranged from 13 to 25° C. and night temperatures of ranged from 7 to 18° C.

Botanical classification: *Petunia×hybrida* cultivar Mariposa Rose.

Parentage:

*Female parent.*—Proprietary selection of *Petunia*× *hybrida* identified as code number 131098, not patented.

*Male parent.*—Proprietary selection of *Petunia*× *hybrida* identified as code number 429, not patented.

Propagation:

*Type cutting.*—Terminal vegetative cuttings.

*Time to initiate roots, summer.*—About 8 to 10 days at 22° C.

*Time to initiate roots, winter.*—About 12 to 15 days at 22° C.

*Rooting habit.*—Numerous, fine, fibrous, and well-branched.

Plant description:

*Form.*—Indeterminate; initially upright, then low spreading and cascading; viscid and glandular pubescent.

*Usage.*—Appropriate for hanging baskets and patio containers.

*Crop time.*—About 8 weeks are required to produce finished flowering plants in 10-cm containers.

*Plant height* (*from soil level to top of plant plane*).—About 18 cm.

*Area of spread.*—About 30 cm.

*Vigor.*—Vigorous; rapid growth rate.

*Branching habit.*—Freely branching with about six lateral branches per plant; removal of terminal apices (pinching) enhances branching.

*Lateral branches.*—Length: About 29 cm. Diameter: About 3.25 mm. Internode length: About 3.75 cm. Texture: Pubescent; viscid, glandular. Color: 144B.

*Foliage description.*—Leaves simple, generally symmetrical and long persisting. Leaf arrangement alternate before flowering, opposite after flowering. Quantity per lateral branch: Typically about 30. Length: About 6.25 cm. Width: About 4 cm. Aspect: Typically horizontal. Shape: Elliptic. Apex: Broadly acute. Base: Attenuate. Margin: Entire. Texture: Very sparse pubescence on both surfaces; glandular, viscid. Color: Young foliage, upper surface: 143A. Young foliage, lower surface: 143B. Mature foliage, upper surface: 146B; venation, 143C. Mature foliage, lower surface: 146C; venation, 146D. Petiole: Length: About 8.5 mm. Diameter: About 3 mm. Color: 146B to 146C.

Flower description:

*Flower type and habit.*—Large-sized flowers; flowers face mostly outward; single, axillary. Flowers persistent. Flowering continuous.

*Natural flowering season.*—Long day responsive; flowering from spring through fall. Plants starting flowering about four to six weeks after rooting.

*Quantity.*—Freely flowering with about 27 flowers and flower buds per plant.

*Fragrance.*—Slight spicy sweet fragrance.

*Flower longevity on the plant.*—About 3 to 4 days.

*Flower buds* (*just showing color*).—Length: About 3 cm. Diameter: About 6.5 mm. Shape: Elongate with slightly flared apices. Color: More gray than 70A.

*Corolla.*—Arrangement/appearance: Single whorl of five petals, fused into flared trumpet. Flower diameter: About 6.75 cm. Flower tube length: About 3.5 cm. Flower throat diameter, distal end: About 1.3 cm. Flower tube diameter, proximal end: About 3 mm. Petal length from throat: About 3.5 cm. Petal width: About 3.2 cm. Petal shape: Rounded, spatulate. Petal apex: Rounded. Petal margin: Entire. Texture: Smooth, velvety. Color: Petal, upper surface, when opening: 67B; veins, 66A. Petal, lower surface, when opening: 70C. Petal, upper surface, opened flower: 67B; veins, 66A; color fading to 72C. Petal, lower surface, opened flower: 67C; veins, 70B to 70C. Flower throat (inside): 75A; veins, 71A. Flower tube (outside): 72C; veins, 148B.

*Sepals.*—Quantity: Five. Shape: Strap-like; narrow; slightly spatulate. Apex: Rounded. Margin: Entire. Texture: Smooth with tiny white hairs. Color: Upper surface: 146B. Lower surface: 146C.

*Peduncle.*—Strength: Moderately strong. Angle: About 45° to stem. Length: About 3.4 cm. Color: 144A.

*Reproductive organs.*—Stamens: Stamen number per flower/arrangement: About five; adnate to corolla tube base. Anther shape: Ovoid. Anther length: About 2 mm. Anther color: 156C. Pollen amount: Scarce. Pollen color: 156C. Pistils: Pistil quantity per flower: One. Pistil length: About 2.2 cm. Stigma shape: Flattened; slightly bi-lobate. Stigma color: 142A. Style length: About 2 cm. Style color: 144C to 144D. Ovary color: 144C.

*Seed.*—Seed production has not been observed.

Disease resistance: Plants of the new Petunia have not been noted to be resistant to pathogens common to Petunia.

It is claimed:

1. A new and distinct cultivar of Petunia plant named 'Mariposa Rose', as illustrated and described.

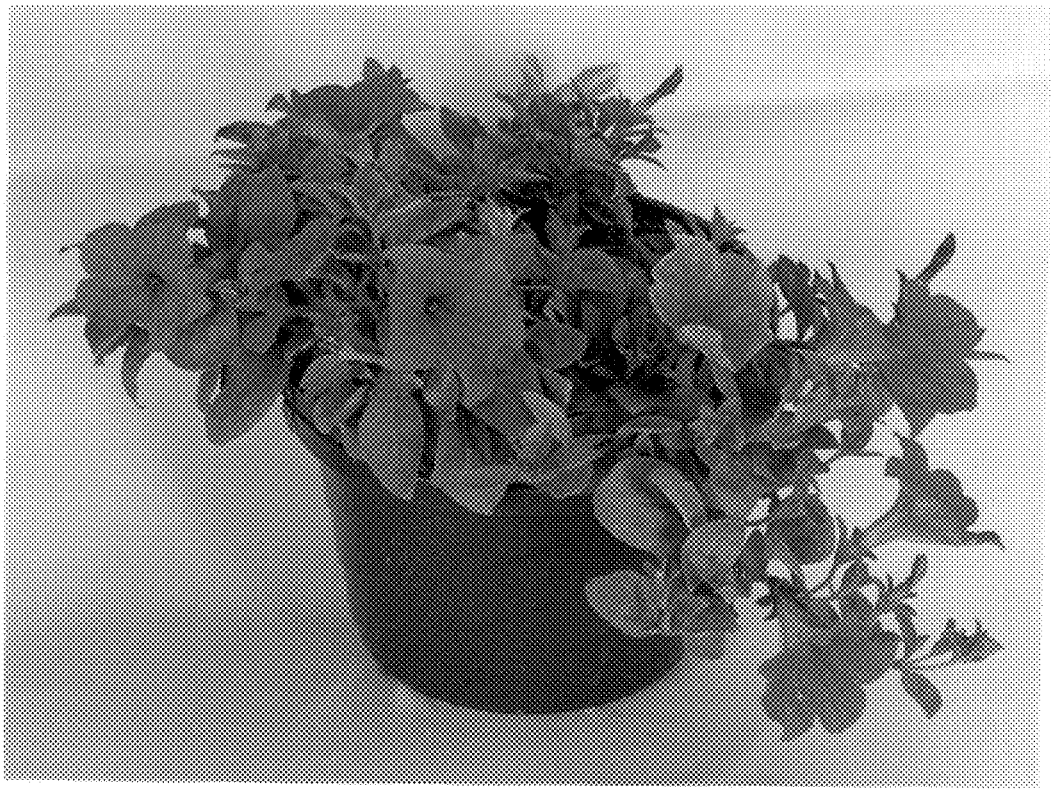
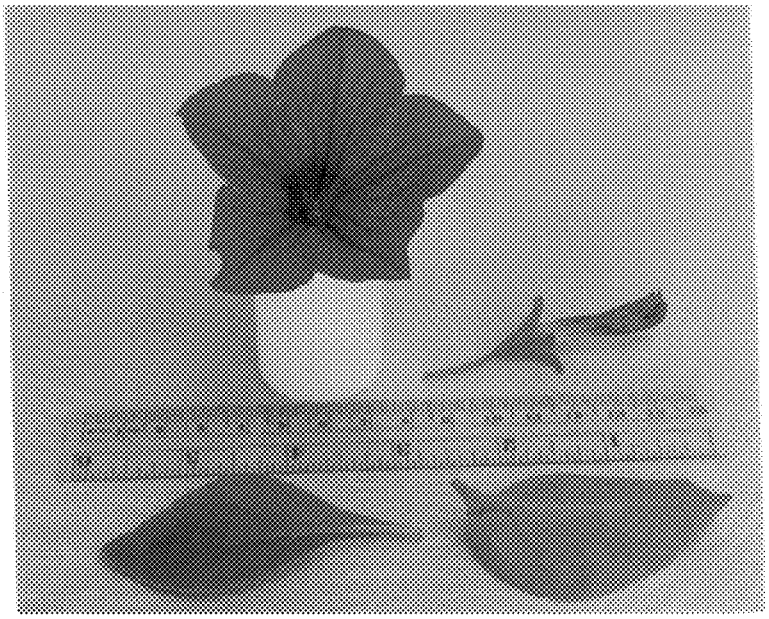

* * * * *